US011986651B1

(12) United States Patent
Williams et al.

(10) Patent No.: US 11,986,651 B1
(45) Date of Patent: May 21, 2024

(54) CARDIAC PACING LEAD

(71) Applicants: Terrell M. Williams, Brooklyn Park, MN (US); Gopi Dandamudi, Gig Harbor, WA (US)

(72) Inventors: Terrell M. Williams, Brooklyn Park, MN (US); Gopi Dandamudi, Gig Harbor, WA (US)

(73) Assignee: The Future of Pacing L.L.C., Brooklyn Park, MN (US)

( * ) Notice: Subject to any disclaimer, the term of this patent is extended or adjusted under 35 U.S.C. 154(b) by 0 days.

(21) Appl. No.: 18/201,140

(22) Filed: May 23, 2023

Related U.S. Application Data

(60) Division of application No. 17/576,380, filed on Jan. 14, 2022, now Pat. No. 11,654,278, which is a continuation of application No. 16/826,007, filed on Mar. 20, 2020, now Pat. No. 11,253,699.

(60) Provisional application No. 62/821,441, filed on Mar. 21, 2019.

(51) Int. Cl.
*A61N 1/05* (2006.01)
(52) U.S. Cl.
CPC .... *A61N 1/0573* (2013.01); *A61N 2001/0578* (2013.01)
(58) Field of Classification Search
CPC ...... A61N 1/057; A61N 1/0587; A61N 1/059; A61N 2001/0578
See application file for complete search history.

(56) References Cited

U.S. PATENT DOCUMENTS

| | | |
|---|---|---|
| 4,991,578 A | 2/1991 | Cohen |
| 5,246,014 A | 9/1993 | Williams et al. |
| 5,306,263 A | 4/1994 | Voda |
| 5,476,497 A | 12/1995 | Mower et al. |
| 5,617,854 A | 4/1997 | Munsif |
| 5,772,693 A | 6/1998 | Brownlee |
| 5,851,226 A | 12/1998 | Skubitz et al. |
| 5,876,385 A | 3/1999 | Ikari et al. |
| 5,964,795 A | 10/1999 | McVenes et al. |
| 5,987,746 A | 11/1999 | Williams |
| 6,004,280 A | 12/1999 | Buck et al. |
| 6,066,126 A | 5/2000 | Li et al. |
| 6,214,016 B1 | 4/2001 | Williams et al. |
| 6,366,819 B1 | 4/2002 | Stokes |
| 6,408,214 B1 | 6/2002 | Williams et al. |
| 6,931,286 B2 | 8/2005 | Sigg et al. |
| 6,937,897 B2 | 8/2005 | Min et al. |

(Continued)

OTHER PUBLICATIONS

Abdelrahman et al., Clinical Outcomes of His Bundle Pacing Compared to Right Ventricular Pacing, JACC vol. 71, No. 20, May 22, 2018, pp. 2319-2330, The American College of Cardiology Foundation, Washington, DC.

(Continued)

*Primary Examiner* — Amanda K Hulbert
(74) *Attorney, Agent, or Firm* — Lund IP PLLC

(57) ABSTRACT

A medical lead includes a lead body, a connector pin proximate to a proximal end of the lead body, a helix extending from a distal end of the lead body, an electrode proximate to the distal end of the lead body, and a cable conductor within the lead body and including an electrode proximate a distal end of the cable conductor, the cable conductor being slideable within the lead body to extend and retract the electrode relative to the distal end of the lead body.

23 Claims, 9 Drawing Sheets

(56) References Cited

U.S. PATENT DOCUMENTS

| | | | |
|---|---|---|---|
| 7,056,294 | B2 | 6/2006 | Khairkhahan et al. |
| 7,082,335 | B2 | 7/2006 | Klein et al. |
| 7,177,704 | B2 | 2/2007 | Laske et al. |
| 7,647,124 | B2 | 1/2010 | Williams |
| 7,657,325 | B2 | 2/2010 | Williams |
| 7,729,782 | B2 | 6/2010 | Williams et al. |
| 8,100,883 | B1 | 1/2012 | Johnson |
| 8,332,042 | B2 | 12/2012 | Williams |
| 8,406,899 | B2 | 3/2013 | Reddy et al. |
| 8,606,369 | B2 | 12/2013 | Williams et al. |
| 8,620,433 | B2 | 12/2013 | Ghosh et al. |
| 8,670,824 | B2 | 3/2014 | Anderson et al. |
| 8,744,579 | B2 | 6/2014 | Parikh et al. |
| 9,504,801 | B2 | 11/2016 | Dangoisse |
| 9,579,501 | B2 | 2/2017 | Shuros et al. |
| 9,662,501 | B2 | 5/2017 | Mongeon et al. |
| 9,700,729 | B2 | 7/2017 | Ghosh et al. |
| 10,737,097 | B2 | 8/2020 | Williams et al. |
| 10,773,087 | B1 | 9/2020 | Williams et al. |
| RE48,319 | E | 11/2020 | Sambelashvili |
| 10,888,354 | B2 | 1/2021 | Kugler et al. |
| 11,253,699 | B1 | 2/2022 | Williams et al. |
| 11,446,486 | B1 | 9/2022 | Dandamudi et al. |
| 11,583,658 | B2 | 2/2023 | Yang et al. |
| 11,654,278 | B1 | 5/2023 | Williams et al. |
| 2003/0130713 | A1 | 7/2003 | Stewart et al. |
| 2003/0204233 | A1 | 10/2003 | Laske et al. |
| 2004/0064158 | A1 | 4/2004 | Klein et al. |
| 2008/0228171 | A1 | 9/2008 | Kugler et al. |
| 2009/0105724 | A1 | 4/2009 | Yoshizaki et al. |
| 2010/0069983 | A1 | 3/2010 | Peacock, III et al. |
| 2010/0179630 | A1 | 7/2010 | Williams |
| 2014/0046389 | A1 | 2/2014 | Anderson et al. |
| 2014/0067036 | A1* | 3/2014 | Shuros .............. A61N 1/0573 606/129 |
| 2018/0078772 | A1 | 3/2018 | Williams et al. |
| 2019/0321625 | A1 | 10/2019 | Shuros et al. |
| 2020/0114146 | A1 | 4/2020 | Foster et al. |
| 2020/0155798 | A1 | 5/2020 | Yang et al. |
| 2020/0261734 | A1 | 8/2020 | Yang et al. |

OTHER PUBLICATIONS

Kawashima et al., A macroscopic anatomical investigation of atrioventricular bundle locational variation relative to the membranous part of the ventricular septum in elderly human hearts, Surgical & Radiologic Anatomy, Feb. 19, 2005, pp. 206-213, vol. 27, Springer-Verlag, Heidelberg, Germany.

Medtronic, C315 Catheter: For the SelectSecure® Pacing lead system, Dec. 2008, Medtronic, Inc., Minneapolis, Minnesota.

Medtronic, HIS—Bundle Pacing Introductory Tutorial, May 2017, Medtronic, Inc., Minneapolis, Minnesota.

Vijayaraman et al., Prospective evaluation of feasibility and electrophysiologic and echocardiographic characteristics of left bundle branch area pacing, Heart Rhythm vol. 16, No. 12, Dec. 2019, pp. 1774-1782, Heart Rhythm Society, Washington, DC.

Kawashima et al., In situ anatomy map provides a new scenario for conduction system pacing, European Heart Journal, Jul. 21, 2023, pp. 2508-2510, vol. 44, Issue 28, Oxford, England.

Medtronic, 6416: Temporary transvenous pacing lead system, Jul. 7, 2015, Medtronic, Inc., Minneapolis, Minnesota.

Medtronic, The SelectSite® Catheter: Giving You Control Where to Place the Lead, Mar. 2007, Medtronic, Inc., Minneapolis, Minnesota.

Nakazato, Safety and usefulness of the Sweet Tip™ type screw-in lead for pacemakers, Journal of Arrhythmia, Apr. 22, 2014, pp. 88-91, vol. 30, Issue 2, Tokyo, Japan.

* cited by examiner

CARDIAC PACING LEAD

RELATED APPLICATIONS

This application is a divisional of U.S. patent application Ser. No. 17/576,380, filed Jan. 14, 2022, which is a continuation of U.S. patent application Ser. No. 16/826,007, filed Mar. 20, 2020, issued as U.S. Pat. No. 11,253,699 on Feb. 22, 2022, which claims the benefit of and priority to U.S. Provisional Application No. 62/821,441, filed Mar. 21, 2019. Each of these applications are hereby fully incorporated herein by reference.

TECHNICAL FIELD

This disclosure relates to cardiac pacing.

BACKGROUND

Typically, pacing leads are deployed to various locations in the heart depending on the nature of the heart condition necessitating the pacing procedure. Conventional ventricular pacing typically involves implanting a lead at the apex of the right ventricle. This placement is still often utilized today even in the face of published evidence of the deleterious effects of bypassing the His/Purkinje system, otherwise known as the cardiac conduction system.

Pacemaker lead electrodes have been regularly placed in or on the heart in a position that bypasses the His/Purkinje system since the inception of pacing in 1957. Conventional pacing directly stimulates the myocardium and has been the standard of care even though His bundle pacing has been known and tried occasionally.

During and around the 1980s, scientific studies found that over time, ventricular pacing resulted in what was termed, "ventricular remodeling," which can result in a number of detrimental effects including: myofiber disarray, fatty tissue and fibrotic deposits away from the electrode, impaired endothelium function, acute hemodynamic compromise, redistribution of myocardial fiber strain and blood flow, with hypertrophy away from the electrode, mitral valve regurgitation due to poor papillary muscle timing, cardiac sympathetic activity, decreases in left ventricle (LV) chamber efficiency, slowing of LV isovolumic relaxation, far LV wall contracting against a closed aortic valve, tricuspid valve insufficiency due to lead mechanical disruption, and mitochondrial abnormality away from the electrode.

By 2002, large controlled studies found that conventional ventricular pacing also resulted in heart failure hospitalization and mortality, especially when the patient was paced forty percent or more or the time. This iatrogenic problem is referred to as "pacing induced heart failure."

In spite of significant research demonstrating significant mortality reductions for His bundle pacing compared to conventional pacing, the value of His pacing has not been widely recognized or practiced among clinicians responsible for implanting cardiac pacing leads and pacemakers.

BRIEF SUMMARY

The inventors believe the limited prevalence of His bundle pacing, and when required, pacing the left bundle branch (LBB) of the conduction system, is in part due to lack of effective leads and lead delivery systems. The cardiac conduction system is comprised in part of His bundle which resides between the atrioventricular (AV) node, and the bifurcation of the LBB and right bundle branch (RBB). These anatomic locations are regarded as difficult targets to reach.

For example, many patients cannot have LBB block corrected by His bundle pacing but can benefit from LBB pacing. Techniques disclosed herein facilitate both His bundle pacing, generally via the septal wall of the right atrium, and LBB pacing, generally via right ventricle (RV) septal access. The present disclosure describes examples of leads and methods for use including delivering a pacing lead to the LBB, at the septal wall of the right ventricle or the His bundle in the right atrium.

Examples of the present disclosure includes a lead with a distal helix to facilitate anchoring to the septal wall of the RV or, alternatively, proximate the His bundle, generally via the septal wall of the right atrium. Such leads may further include a blunt dissection electrode configured for deployment within the septum. The blunt dissection electrode may be advanced to the His bundle or LBB following anchoring the distal end of the lead into the septal wall with the helix. The lead may be implanted via a catheter.

Implantation techniques may include selecting a trajectory for the blunt dissention electrode by manipulating the catheter after anchoring the helix to the septal wall. For example, with the distal end of the catheter-lead assembly anchored to the septal wall, the direction of the trajectory of the blunt dissection electrode may be selected by the clinician by bending the catheter through pushing and pulling from a proximal location outside the body of the patient, as well by rotating the catheter from the outside the body of the patient.

In one example, this disclosure is directed to a medical lead comprising a lead body, a connector pin proximate to a proximal end of the lead body, a helix extending from a distal end of the lead body, an electrode proximate to the distal end of the lead body, and a cable conductor within the lead body and including an electrode proximate a distal end of the cable conductor, the cable conductor being slideable within the lead body to extend and retract the electrode relative to the distal end of the lead body.

In another example, this disclosure is directed to a method for implanting a medical lead, the method comprising anchoring a helix of the medical lead to a patient tissue proximate a target site, and extending a cable conductor from a lead body of the medical lead to deploy an electrode within the patient tissue.

DETAILED DESCRIPTION

Figure 1:
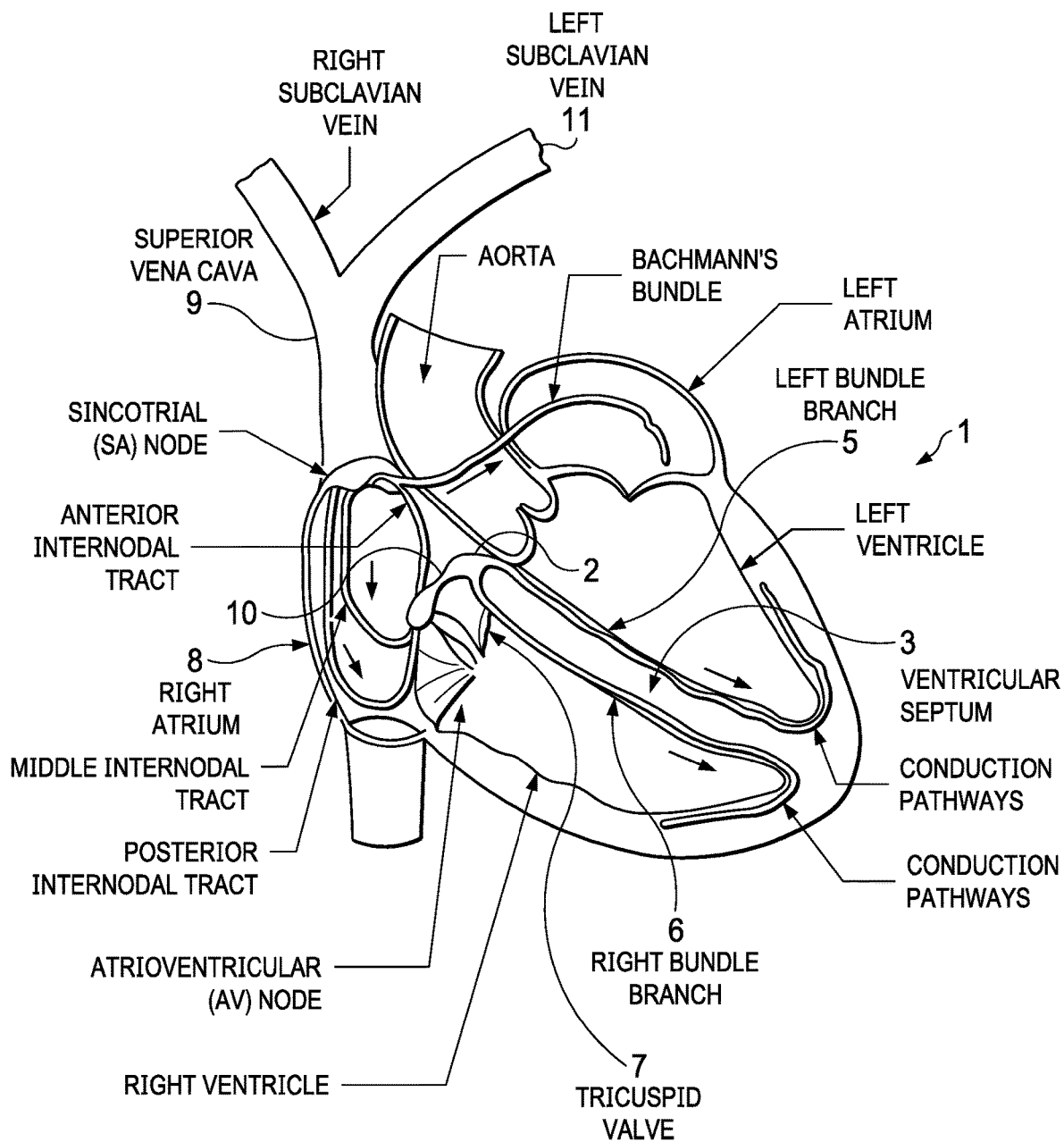
FIG. 1 is a cross-sectional illustration of a human heart depicting the anatomy of the heart and its electrical system.

The prevalence of His bundle pacing, though increasing, is practiced in a small minority of pacing lead implantations both in the United States and worldwide. The His bundle presents a small target and is hard to reach successfully. This increases "fluro time" which is a detriment to both patient and the surgical clinician. However, in one study by the inventors, the mortality rate of one hospital doing conventional pacing was compared with the mortality rate with another hospital doing pacing at the His bundle (for normal physiological ventricular activation). Heart failure and patient mortality was lower at the hospital providing physiological ventricular activation by His bundle pacing.

It is generally more difficult to place a cardiac lead electrode at the conduction system for His bundle pacing than it is to place within the ventricle for conventional pacing. However, techniques of the present disclosure mitigate difficulties with locating a lead electrode to capture the His bundle. Disclosed techniques also facilitate locating a lead electrode to capture the LBB, which is important for patients with LBB block in which the capturing the His bundle may not provide effective LBB normalization.

In one example, a lead includes a helical anode anchor configured to be anchored on the septum of the right atrium, piercing the endocardial membrane of the right atrium. The cathode is connected via a cable conductor extending from the connector end of the lead. A clinician advances the cable conductor through the coaxial center of the lead, advancing the cathode via the pierced endocardial membrane of the right atrium to a targeted portion of the cardiac conduction system, usually the His bundle within the septum or extending distally to the LBB.

The trajectory of the cathode is controlled by the angle of the lead delivery catheter following anchoring of the helical anode anchor. While anchored, the clinician may manipulate the angle of lead delivery catheter. The catheter pivots the helical anode, controlling the trajectory of the cathode.

In this manner, the catheter and fixation screw need not be presented at any particular angle (such as perpendicular) to the endocardial surface. The trajectory of the cathode can be manipulated after anode fixation and has no bearing on His pacing threshold. Thus, a variety of lead delivery catheters may be suitable for delivery of leads disclosed herein.

Once the clinician is satisfied with the angle of the catheter, the clinician advances the cable, having the cathode electrode attached at the distal tip, is advanced from the connector end, through the lead body and helical anode to the targeted portion of the cardiac conduction system, e.g., via blunt dissection. In other examples, the tissue may be cut with a sharp electrode or RF energy. However, blunt dissection may provide an advantage of mitigating the risk of piercing the septum as the endocardial membrane of the ventricular septum provides a relatively durable and elastic layer resistant to blunt dissection compared to the muscular central portion of the ventricular septum.

Selection of either specific or nonspecific His bundle pacing can be achieved for type two His anatomy because of the cathode is small enough to fit within the His bundle. Type two His anatomy, existing in an estimated 32% of patients, is where the His bundle dives below the central fibrous body and is surrounded by myocardium. Large electrodes, such as helical electrodes of current leads may be too large to exclude the myocardium from activation along with the His bundle (called non-specific His bundle pacing). In contrast, smaller electrodes of leads disclosed herein, such as those with an electrode radius of about 0.5 mm, allow for "specific" His bundle pacing. Such smaller electrodes may also facilitate LBB pacing, in the event that LBB block cannot be corrected at the His bundle due to infrahisian block, e.g., through trans-septal lead placement.

In contrast, a clinician attempting to use a conventional screw-in lead meant for right ventricle or atrial endocardial attachment may try to drill thru the septum-a process that is very tedious, reportedly requiring at times, forty turns, and having the risk of penetration into the lumen of the left ventricle risking embolic stroke.

FIG. 1 shows the cardiac anatomy, especially the cardiac conduction system. In a healthy heart, the natural pacemaker, the SA node, activates the high conduction velocity Purkinje fibers within the right and left atria, resulting in coordinated atrial muscle cell contraction. This injects blood collected in the atria, into the powerful left and right ventricles. There is a pause in conduction at the AV node allowing the ventricles to fill. Then, just before blood flows back into the atria, the AV node activates the His bundle and, by high conduction velocity, the left and right bundle branches and the entire Purkinje system. This choreographs ventricular contraction, endocardial myocardium contracting first followed by epicardial muscle contraction. This programmed ventricular muscle activation produces an efficient pumping action that not only squeezes blood out of the ventricles but produces kinetic energy as blood is accelerated from the ventricles. The result of conventional pacing is compromised Hemodynamics due to slow cell-to-cell conduction and an aberrant ventricular activation sequence as the cardiac conduction system is bypassed. The far-left ventricular wall away from the electrode site has been seen contracting against an already closed aortic valve.

For contextual understanding, of how examples of the disclosure are intended to function, FIG. 1 is included to illustrate the structure of a typical human heart 1 with relevant anatomical features shown. As mentioned, one example of the disclosure is directed to a method for deploying an electrical lead to the His bundle 2 at a target site 10 along the septum 3 distal to the atrioventricular (AV) node 4, but proximal to the left bundle branch (LBB) 5 and the right bundle branch (RBB) 6. Such a target site 10 for proper deployment of a pacing lead, is depicted in FIG. 1 at the crest of the ventricular septum 3 on the atrial aspect of the annulus of the tricuspid valve septal leaflet 7 within the right atrium 8.

In some patients, such as those experiencing LBB block, the target site is instead the LBB 5, potentially be accessed from target site 10, or from an alternative target site on ventricular septum 3 from within the right ventricle.

Figure 2:
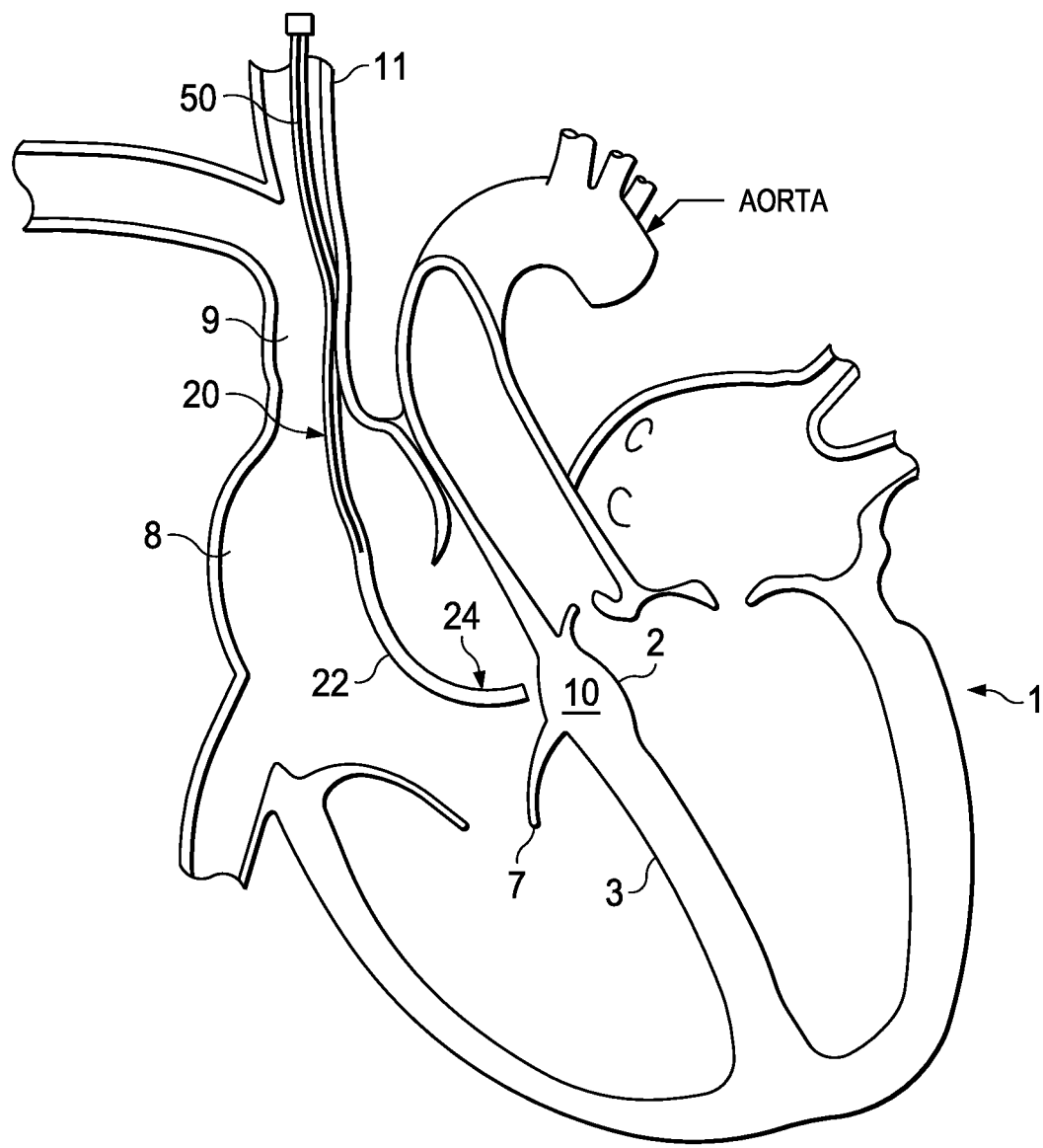
FIG. 2 is a cross-sectional illustration of a human heart wherein an example of a guide catheter is shown advanced to a target site within the central fibrous body, between the tricuspid valve and the aortic valve and corresponding to the His bundle.

FIG. 2 is the schematic diagram of FIG. 1 in which a distal portion or end region 22 of delivery catheter 20 is shown extending into the right atrium 8 of the heart 1, from the superior vena cava 9 and the left subclavian vein 11, with the distal tip 24 positioned at the target site 10.

Typically, left pectoral side approach is desired. It involves accessing the heart via the left subclavian vein, the cephalic vein and more rarely the internal or external jugular vein, or femoral vein. However, it is also possible to utilize the less common right pectoral side approach. In either case, for catheter lead placement, a guide wire 50 may be advanced into the heart 1 from the access site. Delivery catheter 20 may be advanced through the vasculature and into the heart 1 over the guidewire; once in position the guidewire is removed. A pacing lead is then advanced through the guiding catheter 1 to be deployed at various regions in the heart.

Figure 3:
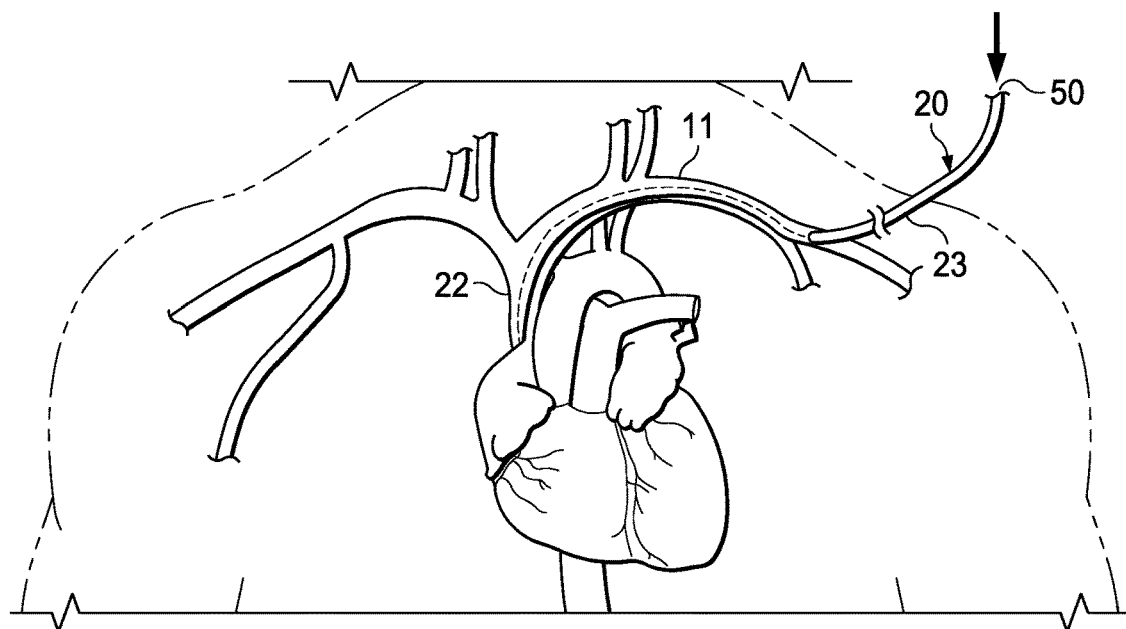
FIG. 3 is an anatomical illustration of a patient and the manner in which the example shown in FIG. 2 initially accesses the vasculature prior to advancement into the heart.

According to one method, a clinician positions guide wire 50 into the heart 1, for example via a "sub-clavian stick" or central venous access procedure such as is illustrated in FIG. 3. Accordingly, the catheter 20 is passed over the guide wire and advanced into the superior vena cava 9 from the left subclavian vein 11 and into the right atrium 8 such as is in the manner shown in FIG. 2.

Figure 4:
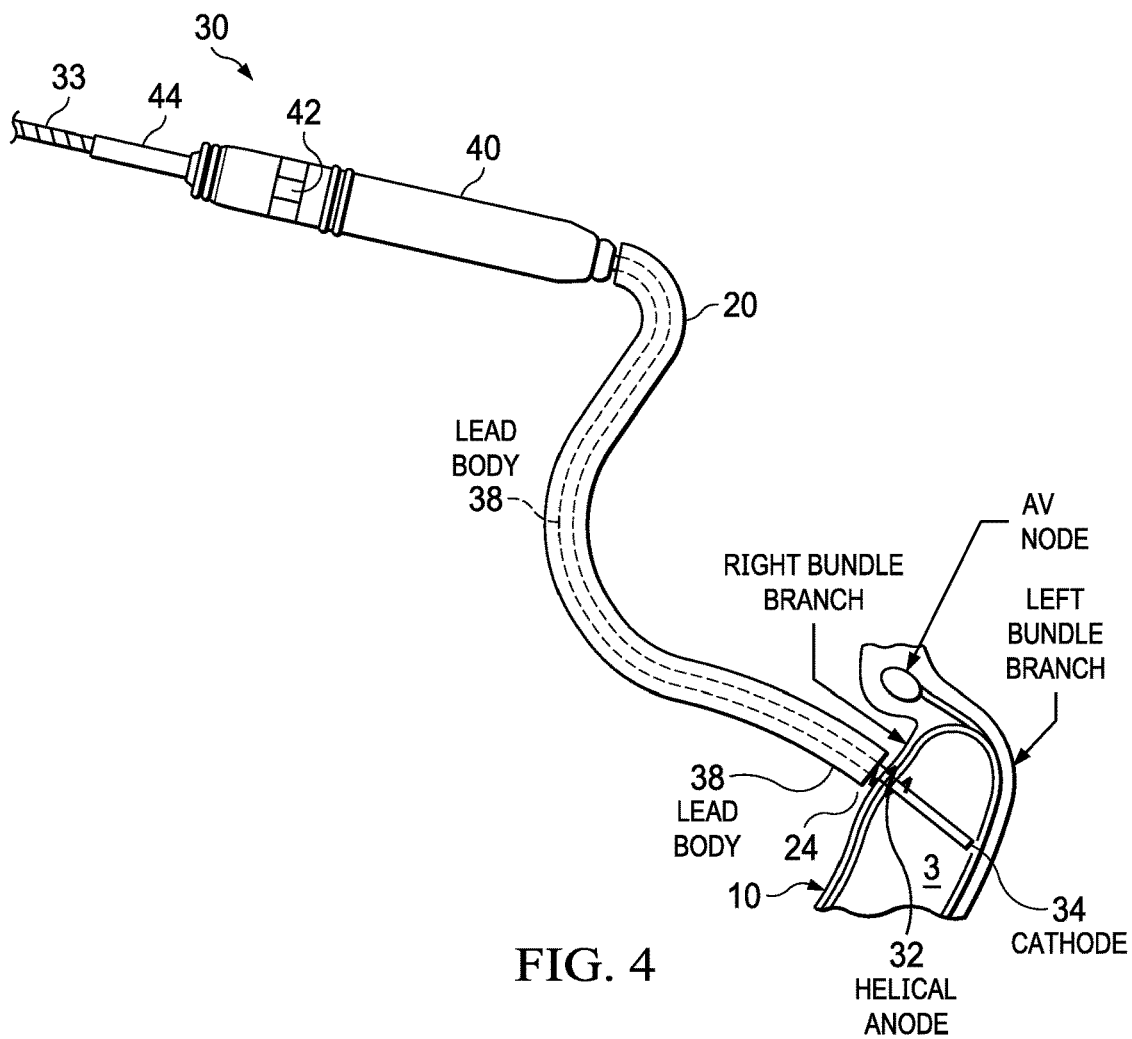
FIG. 4 is a conceptual illustration of a pacing lead accessing the septum from the RV in accordance with one example of this disclosure.

FIG. 4 illustrates a medical electrical lead 30 in accordance with one example of this disclosure. Medical electrical lead 30 includes a central cable conductor 33 terminating at cathode electrode 34 and extending within a central lumen of lead 30 about a length of lead body 38 for coupling to connector pin 44 of proximal connector 40.

Cable conductor 33 includes one or more conductive elements forming an electrical connection between cathode electrode 34 and connector pin 44, once connector pin 44 is connected to the conductive elements of cable conductor 33. In various examples, cable conductor 33 may include a solid wire conductor, a stranded wire, or a coil conductor. In a particular example, cable conductor 33 may include a fiber core coil with one or more electrically conductive wires coiled on a fiber core. The fiber core may provide tensile strength for cable conductor 33 and mitigate stretching of the coiled conductors during retraction of cable conductor 33.

In the same or different examples, cable conductor 33 may be an insulated cable conductor including outer insulating layer, leaving the distal tip exposed for cathode electrode 34. The insulating layer may include silicone rubber, polyurethane parylene, polymide and/or ethylene tetrafluoroethylene (ETFE) cable insulation. In some examples, connector pin 44 may be a self-stripping connector pin 44 to allow contact with the conductive elements of cable conductor 33. Alternatively, connector pin 44 may make electrical contact with conductive elements of cable conductor 33 upon tightening of a setscrew of the connector of a pulse generator or other device connected to proximal connector 40. Central cable conductor 33 is slideable the central lumen of lead body 38 to extend and retract cathode electrode 34 relative to the distal end of lead body 38.

In the same or different examples, cathode electrode 34 may be a unitary component with the conductive element(s) of cable conductor 33, or may be a separate component physically and electrically coupled to the distal end of the conductive element(s) of cable conductor 33, for example, by solder or welding, such as laser welding. In some examples, the cathode electrode 34 is a 0.5 to 2.0 mm diameter, such as 0.7 to 1.0 mm diameter hemispherical electrode, such as a half sphere with a diameter of about 0.87 mm, at the end of an insulated cathode conductor of the same diameter in order to provide blunt dissection.

Medical electrical lead 30 further includes a second conductor within lead body 38 extending between ring terminal 42 and helix anode electrode 32. In some examples, the second conductor is a coil conductor surrounding the central cable conductor 33 within the lead body 38.

Helix anode electrode 32 may be made from a wire. The number of turns and length of the helix may be adapted for a particular application. For example, helix anode electrode 32 may have 1 to 8 turns, such as 2 to 4 turns to support adequate fixation within patient tissue. A septal thickness can be anywhere from 0.9 cm to 1.2 cm in normal individuals. A risk of perforation will likely go up if the helix is too long and the entire helix penetrates the septum. Accordingly, the dimensions of the helix should be selected to allow fixation but mitigate a risk of perforation. In the present example, a helix length of 1.0 to 8.0 mm may be appropriate to mitigate a risk of piecing the septum, such as a helix length of 1.5 to 4 mm, such as about 1.8 mm. As used herein, the term about means within a range of tolerances of manufacturing techniques used to produce the referenced element. Moreover, the length of helix anode electrode 32 should be selected to provide a suitable distance between helix anode electrode 32 and cathode electrode 34 to support stimulation with helix anode electrode 32 and cathode electrode 34.

In one particular example of lead 33 the following dimensions may be used. Lead body 38 diameter 3 to 6 French, such as about 4.1 French, cable conductor 33 diameter, 0.02 to 0.05 inches, such as about 0.028 inches, helix 32 length 1 to 4 mm, such as about 1.8 mm, helix 32 pitch, 0.5 to 2 mm, such as about 1 mm, helix 32 wire diameter 0.006 to 0.03 mm, such as about 0.012 mm. In the same or different examples, the following materials may be utilized for the helix anode electrode 32 wire: Pt 80%/Ir 20% or Pt 90%/Ir 10% for a thinner wire.

As used herein, the terms anode and cathode merely represent example uses of particular lead electrodes. For example, anode electrode 32 and cathode electrode 34 are electrically isolated within medical lead 30 such that such that anode electrode 32 and cathode electrode 34 may form an electrode pair to deliver stimulation. However, the polarity of the stimulation is controlled by a pulse generator and not inherent to the structure of electrical lead 30 itself. Thus, the pulse generator could reverse the polarity of anode electrode 32 and cathode electrode 34, or even use one or both of anode electrode 32 and cathode electrode 34 in combination with the pulse generator housing. For example, one or both of anode electrode 32 and cathode electrode 34 could be configured as a cathode while the pulse generator housing serves as the cathode.

In FIG. 4, a close-up view of the distal tip 24 of the catheter 20 is shown following advancement of medical electrical lead 30 though a lumen of the catheter 20 to the target site 10. In this example, the target site is the LBB, although the His bundle can also be targeted.

The lead 30 is extended distally from distal tip 24 and anchored into the septum 3 by clockwise rotation of the lead body 38 targeting the LBB, so that helical anode electrode 32 screws through the endocardial membrane and into the septal wall. The cathode electrode 34 is extended into the septum 3 to provide pacing to the heart 1 via the LBB. In some examples, cathode cable conductor 33 and cathode electrode 34 may extend through the hole in the endocardial membrane created by helical anode electrode 32. In other examples, RF energy may be applied to cathode cable conductor 33 to cross the RV endocardium, then detaching the RF connection to cathode cable conductor 33 and advance it to the LV endocardium. The preferred method of advancement is via blunt dissection.

Figure 5A:
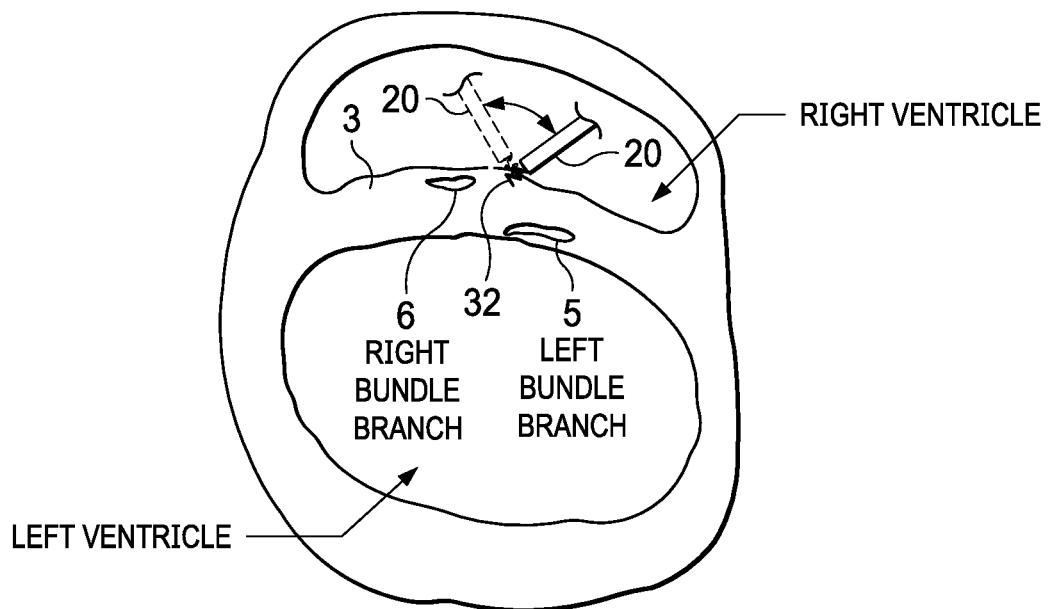
FIGS. 5A-5C illustrate detailed views of the distal region and tip of the pacing lead while mapping the LBB while attached to and fixed in a patient's septum.
Figure 5B:
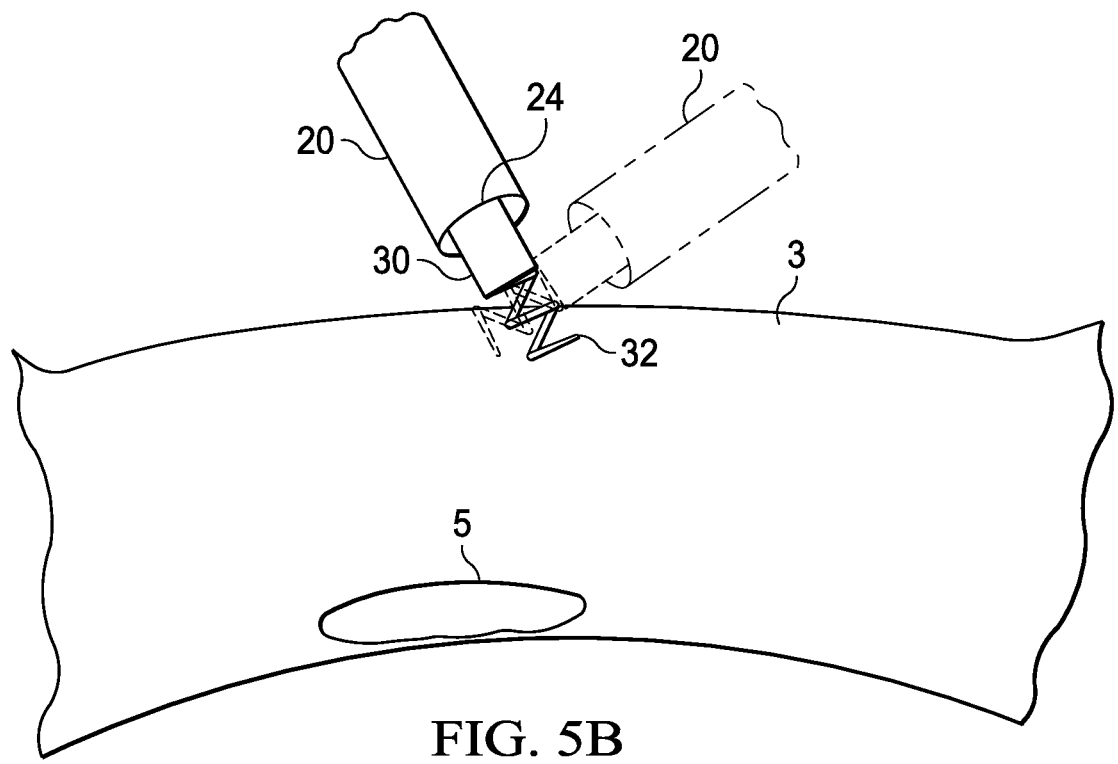
Figure 5C:
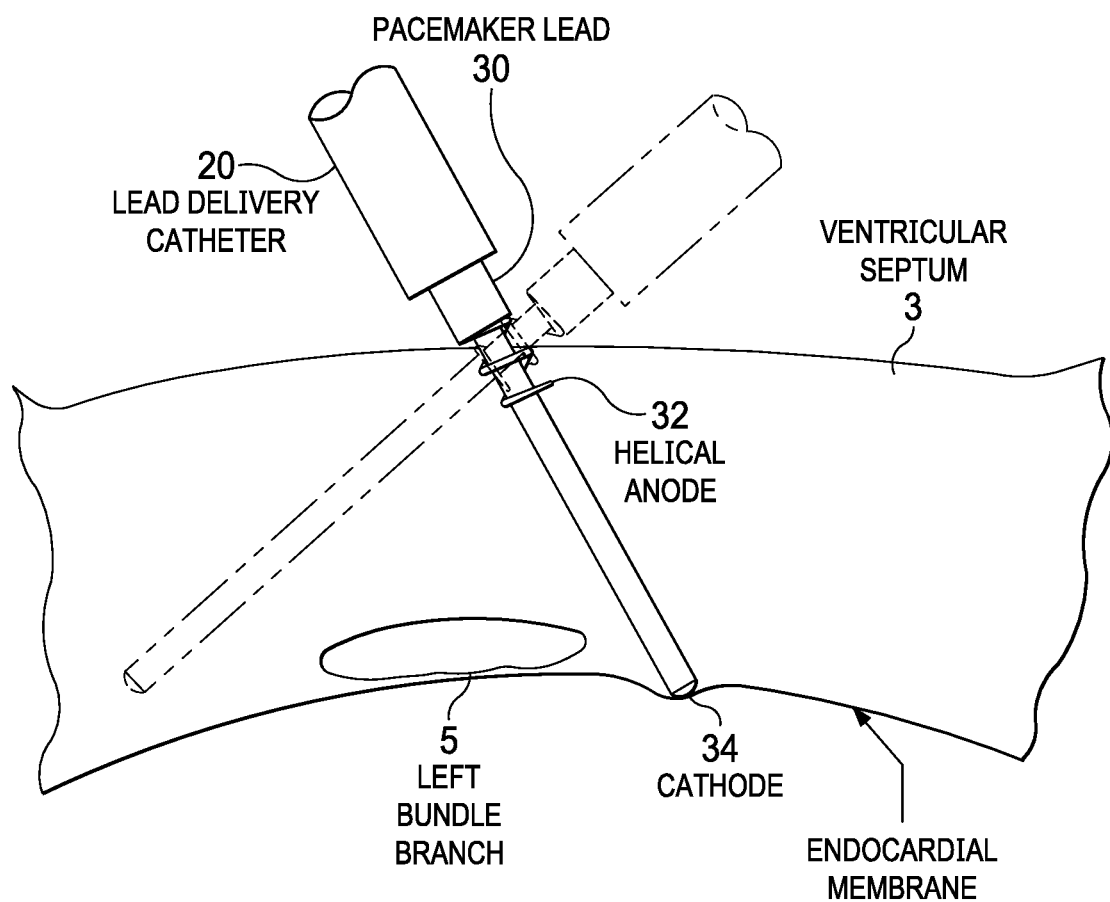

FIGS. 5A-5C illustrate detailed views of the distal region and tip of the pacing lead at a target site in a patient's septum. Specifically, FIG. 5A shows the trajectory of the cathode direction for mapping of the LBB during catheter introduction of the lead 30, while FIG. 5B shows a closeup of the lead delivery catheter and lead tip. The helix anode electrode 32 for lead attachment is shown anchored and is pivoted by the lead delivery catheter.

FIG. 5C shows the LBB mapping process and possible range of cathode location. Mapping for lead location is accomplished by sensing the LBB potential and/or pacing the LBB to produce a narrow QRS on the surface ECG, typical of physiologically normal ventricular activation. The trajectory of the cathode advancement is controlled by manipulation of the lead delivery catheter. Resistance to advancement of cable conductor 33 is felt when the electrode 34 impinges on the tough left ventricular endocardial membrane. See the tenting effect of the opposite endocardial membrane in FIG. 5C.

Figure 6:
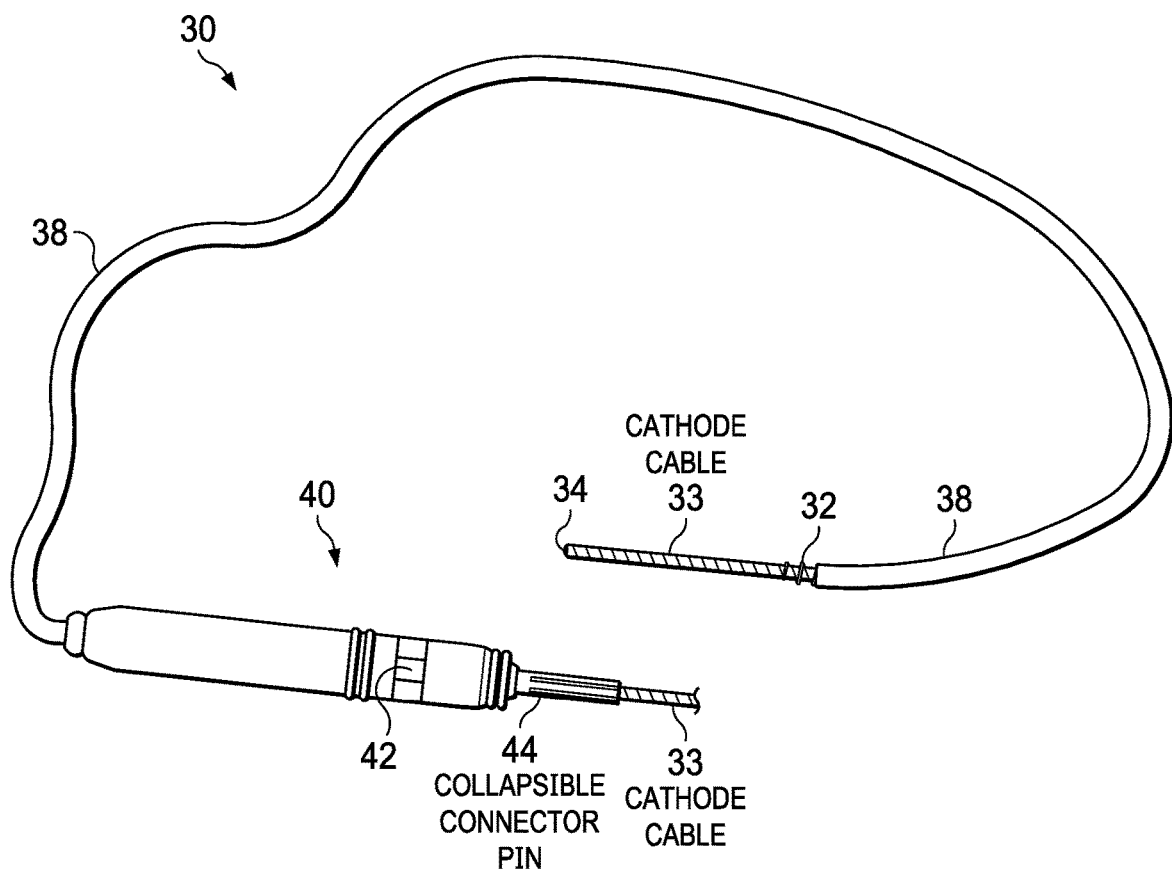
FIG. 6 illustrates the pacing lead with the proximal blunt dissection conductor and a self-stripping connector pin.

FIG. 6 illustrates lead 30 including a proximal connector 40 with a self-stripping connector pin 44. After selecting a proper lead position in the heart, cathode cable conductor 33 is cut flush with the connector pin 44. The pulse generator's connector setscrew is tightened to make electrical contact, fracturing the cable insulation and completing the circuit to cathode electrode 34. Also illustrated is proximal ring terminal 42, located adjacent and distal to connector pin 44. Ring terminal 42 provides an electrical connection to anode electrode 32.

The example proximal connector 40 illustrated in FIG. 6 conforms to the IS-1 standard. In various examples, connector 40 may conform to a standard pulse generator connector, such as an IS-1, IS-4, DF-1, DF-4 or other industry standard connector.

Figure 7A:
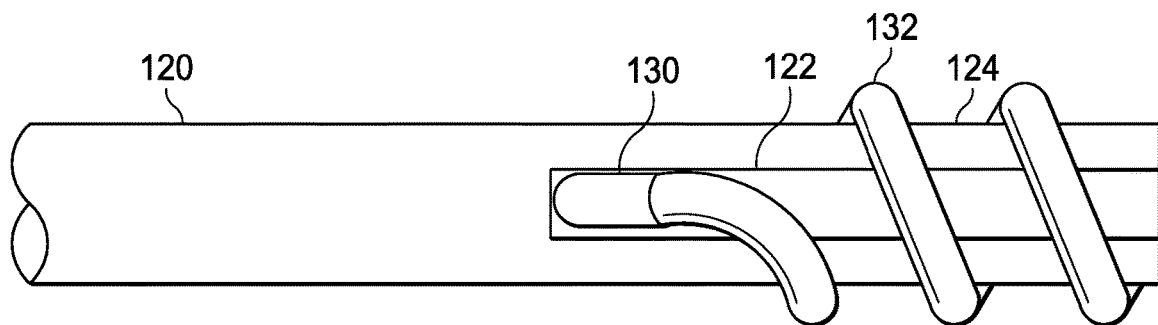
FIGS. 7A-7C illustrate an alternative lead design with an exposed helical electrode that facilitates mapping.
Figure 7B:
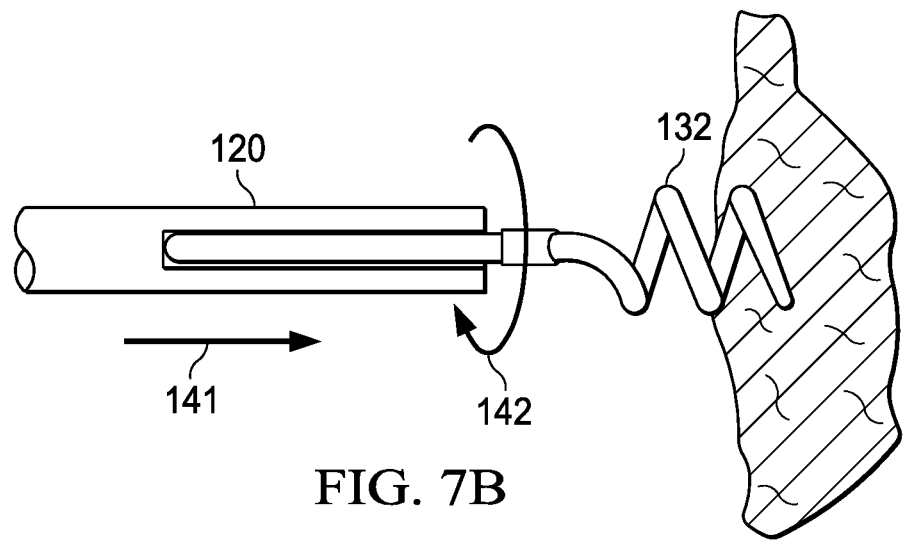
Figure 7C:
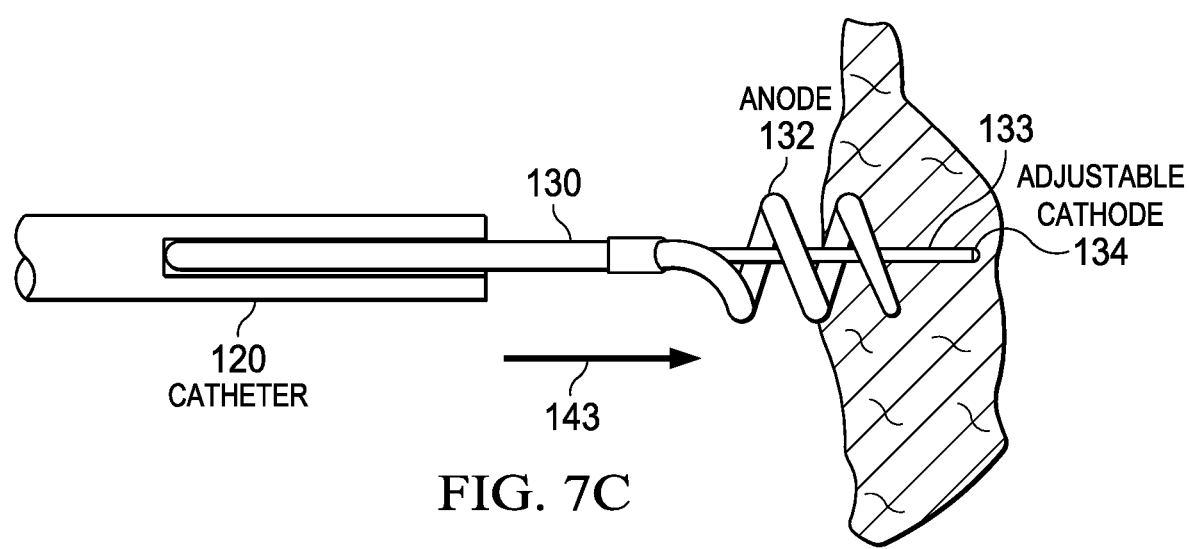

FIG. 7A-7C illustrate the distal end of a medical electrical lead 130, which provides an alternative lead design as compared to medical electrical lead 30. With this example, an anode helix 132 is attached over the lead delivery catheter tip 124. This exposes the anode 132 for mapping purposes. As shown in FIG. 7A, anode helix 132 extends through slot 122 which extends along a length of delivery catheter 120 at lead delivery catheter tip 124. The pointed distal tip of anode helix 132 is closely fitted to the catheter outer diameter to prevent snagging on inter-vascular tissue during venous passage of the catheter lead assembly. Deployment of anode helix 132, e.g., by extending in direction 141, then turning lead 130 relative to the patient tissue in direction 142 (corresponding to the curvature of anode helix 132) anchors the distal tip of anode helix 132 in the patient tissue.

Similar to lead 30, lead 130 includes a blunt dissection electrode 134, the trajectory of which is selectable by a clinician by manipulating the catheter lead assembly after anchoring helical anode 132 within a tissue of the patient, such as the septal wall. This design of catheter 120 and lead 130 may increase the percutaneous introduction size, such as by 2 French as compared to catheter 20 and lead 30. Following the selection of the trajectory, the clinician may deploy electrode 134 within the patient tissue along direction 143, representing the selected trajectory, by pushing cable conductor 133 relative to anode helix 132 of lead 130.

Figure 8:
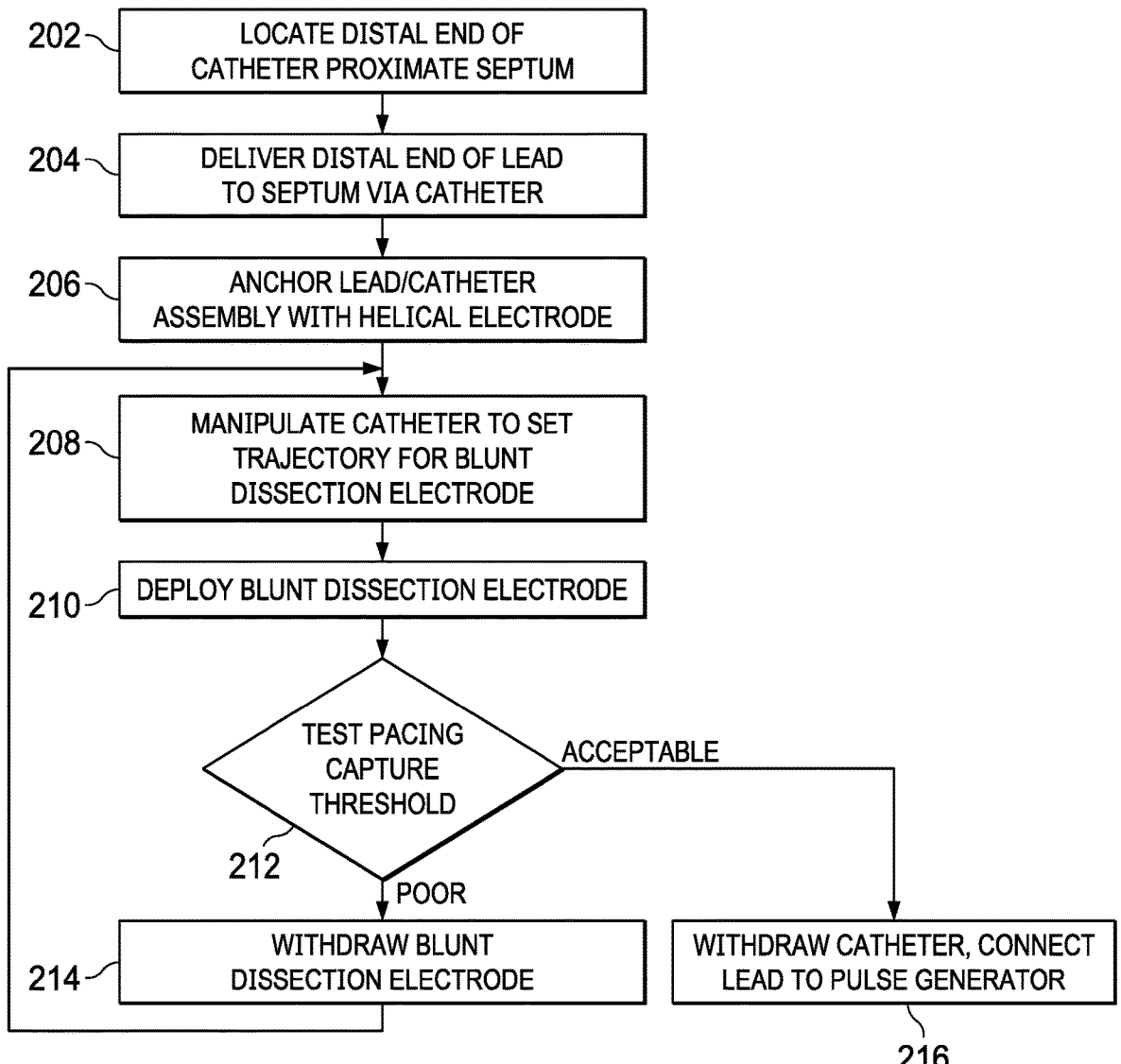
FIG. 8 is a flowchart illustrating techniques for locating a lead electrode proximate the His bundle.

FIG. 8 is a flowchart illustrating techniques for locating a lead electrode to pace the cardiac conduction system, either the LBB or proximate the His bundle. For clarity, the techniques of FIG. 8 are described with respect to catheter 20 and medical electrical lead 30, although the techniques may likewise be applied to medical electrical lead 130 and to variations of the example leads disclosed herein.

First, a clinician positions the distal tip 24 of catheter 20 at the target site 10 on a patient's septum or proximate the His bundle (202). In some example, a guidewire may be used to direct the catheter to target site 10. Once, the distal tip 24 of catheter 20 is positioned at the target site 10, the clinician removes guidewire (if any) and introduces lead 30 via the central lumen of the catheter 20. The distal end of lead 30 is delivered to the target site 10 in the septum via catheter 20 (204). In other examples, lead 30 may be introduced with a stylet, after temporarily extracting the central cable conductor 33 from the central lumen of lead 30. The relatively stiff stylet may also be used by, blunt dissection, to clear a pathway through tough tissue such as the central fibrous body or along the left ventricular septum paralleling the LBB, especially when a relatively flexible cable conductor 33 is desirable.

The clinician anchors the catheter lead assembly to the target site 10 in the septum by rotating the lead 30 to engage the septum with the helical electrode 32 of lead 30 (206).

The clinician may then manipulate the catheter 20 to set a desired trajectory for blunt dissection of the septum with the blunt dissection cathode electrode 34 (208). For example, the clinician may select a trajectory for the blunt dissention electrode by manipulating the catheter after anchoring the helical electrode to the septal wall by bending the catheter through pushing and pulling from a proximal location outside the body of the patient, as well by rotating the catheter from the outside the body of the patient. Once helix anode electrode 32 is fixed to the septum, the cathode can be advanced, by blunt dissection (210), at least 1.8 cm from the base of helix anode electrode 32, toward the left bundle branch, just inside left ventricular septum.

For mapping, the clinician may optionally withdraw the blunt dissection electrode 34 (214), set a new desired trajectory, and redeploy the blunt dissection electrode 34. Generally, however, a clinician will only want to reset the position of blunt dissection electrode 34 if the capture threshold is undesirable (212). If mapping finds adjustment is necessary, cathode electrode 34 is extracted to helix anode electrode 32 and helix anode electrode 32 can be pivoted to a desired new trajectory for advancement of cable conductor 33.

For example, with His bundle pacing, pacing threshold voltage is generally greater than that of conventional pacing, but current threshold is generally less than that of the electrode of conventional pacing leads having higher electrode surface area, thus lower pacing impedance, so that the battery drain is comparable or better than with to conventional pacing. Cathode pacing impedance may be on the order of 1,000 ohms.

In some examples, the cathode electrode 34 is a 0.7 to 1 mm diameter hemispherical electrode at the end of an insulated conductor of the same diameter in order to provide blunt dissection. This relatively small surface area (of about one square mm) for the exposed electrode may provide one or more advantages. For example, the smaller area may facilitate a reduced battery drain. Micro-dislodgement issues with other small pacing electrodes should be limited due to the embedded myocardial electrode placement of cathode electrode 34 as opposed to placement on the endocardial surface as is the case for conventional tined leads. Thus, the disclosed techniques may mitigate instances of micro-dislodgement as can occur with electrodes positioned on the surface of a patient tissue.

In the same or different examples, the hemispherical tip electrode 34 of cathode cable conductor 33 may be coated with a steroid to mitigate scar tissue and its negative effects on capture threshold over time.

Occasionally, His bundle pacing (at the tip of the ventricular septum and within the right atrium) cannot correct LBB block. LBB block cannot be corrected by His bundle pacing in as many as 30-40% of patients due to infra-hisian block. When that happens, cable conductor 33 may be retracted and the trajectory of cable conductor 33 adjusted to target the LBB. Specifically, the clinician may target the LBB from with the right atrium without repositioning the anode helix, rather than from the RV as described previously. In such examples, the previously anchored anode helix can be pivoted about ninety degrees to align with the ventricular septum. When cable conductor 33 is advanced, cathode electrode 34 slides along the endocardial membrane of the left ventricle, targeting the LBB, thereby bypassing the infra-hisian block.

When used for His pacing, particularly when the left bundle branch block cannot be corrected at the His bundle due to distal block, cathode electrode 34 is retracted to the anode helix. The helix is rotated to a cathode trajectory that aims at the left bundle branch. The cathode is then advanced along the left ventricular endocardial membrane to pace the left bundle branch.

Once the position of the blunt dissection electrode 34 is satisfactory, the clinician may withdraw catheter 20, cut the cable conductor 33 flush with connector pin 44, insert proximal connector 40 into the pulse generator's connector, and tighten the set-screw to cut through the insulation and complete the circuit (216). In examples in which the pulse generator is an implantable pacemaker, the clinician then inserts the implantable pacemaker in a pocket under the skin in the patient's chest and is ready for sensing and/or pacing via the lead 30.

Figure 9:
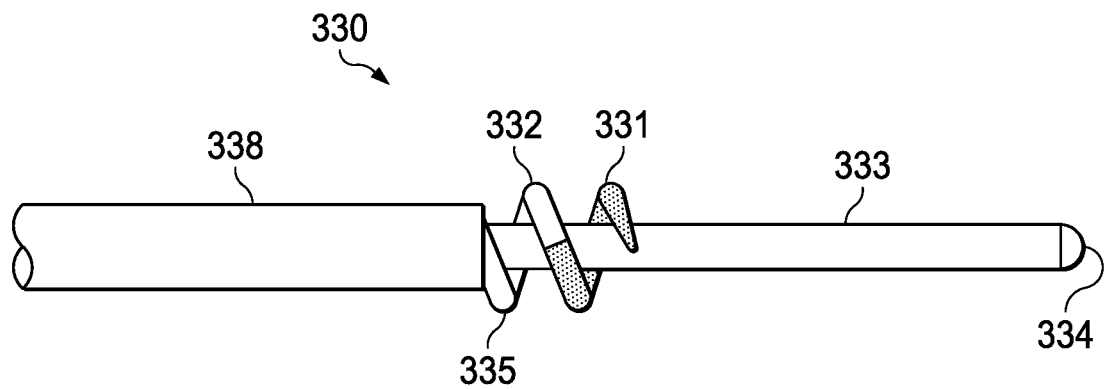
FIG. 9 illustrates an alternative lead design with a helix partially covered by an insulating layer.

FIG. 9 illustrates medical electrical lead 330. Lead 330 is substantially similar to lead 30 except that lead 330 includes an insulating layer 331 over the distal portion of helix anode 332, partially covering helix anode 332. The insulating layer 331 limits the exposed anodal surface area 335, increasing field density adjacent anode 332 to allow for bifocal stimulation. In all other aspects, lead 330 is the same as lead 30. For brevity, details discussed with respect to lead 30 are discussed in limited or no detail with respect to lead 330.

Medical electrical lead 330 includes a central cable conductor 333 for a cathode 334, as well as a second conductor for anode 332. In some examples, the anode conductor is a coil conductor surrounding the cathode conductor within the lead body 338. In the same or different examples, the cathode conductor may be an insulated conductor, such as a solid wire, a stranded wire, or a coil conductor.

In some examples, the cathode 334 is a 0.5 to 2 mm diameter, such as 0.7 to 1 mm diameter hemispherical electrode, such as a half sphere with a diameter of about 0.87 mm, at the end of an insulated cathode conductor of the same diameter in order to provide blunt dissection. In the same or different examples, the following materials may be utilized for the helix anode 332 wire: Pt 80%/Ir 20% or Pt 90%/Ir 10% for a thinner wire. In the same or different examples, the insulating layer 331 over anode helix 332 may be any suitable dielectric material, such as a polymer material, such as silicone rubber, polyurethane, parylene, polymide and/or ETFE or other non-conductive material.

The configuration of lead 330 provides reduced anodal pacing threshold compared to lead 30. Such a configuration may be particularly useful when right septal bifocal stimulation is desired for example. Such pacing may be useful to support LV/RV synchronization. The configuration of lead 330 is also suitable for His bundle pacing near the endocardial surface by prevention of cathode shorting to the helical anode as may occur with lead 30.

Figure 10:
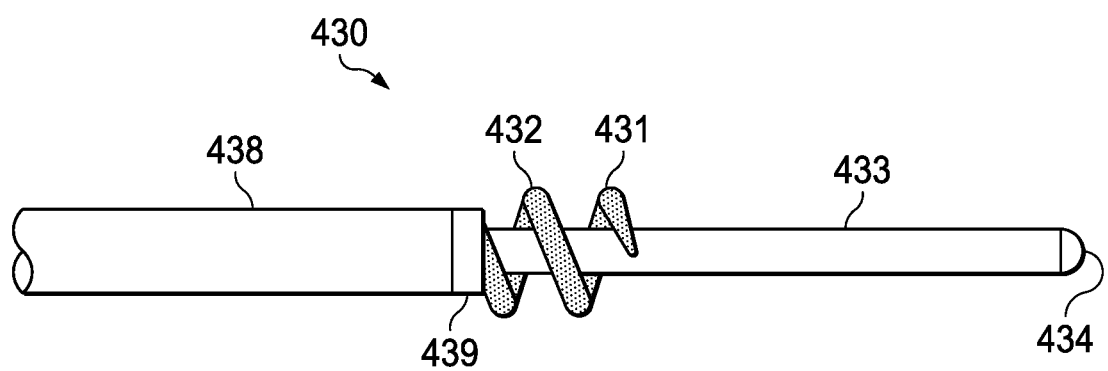
FIG. 10 illustrates an alternative lead design with a insulated helix fully covered by an insulating layer and an anode ring on the distal end of the lead body.

A ratio of anode to cathode surface area should be selected to support bifocal pacing. In some examples, the anode to cathode area ratio should be in 1:1 to 4:1, such as 1.5:1 to 3:1 such as about 2.3:1. In one particular example of lead 330 the following dimensions may be used. Lead 330 diameter 4.1 F, cable conductor 333 diameter 0.028 inches, helix 332 length 1.8 mm, helix 332 pitch 1 mm, helix 332 wire diameter 0.012 mm, cathode 334 surface area 1.2 mm$^2$, exposed anode 335 surface area 2.8 mm$^2$ FIG. 10 illustrates medical electrical lead 430. Medical electrical lead 430 includes an insulating layer 431 fully covering portion of helix 432. Medical electrical lead 430 further includes an anode ring electrode 439 on the distal end of lead body 438. In other examples, ring electrode 439 may be partial ring electrode. In the same or different examples, helix 432 is laser welded to ring electrode 439. In the same or different examples, ring electrode 439 may be on a distal portion of lead body 438, but not necessarily on the distal tip of lead body 438. Lead 430 is otherwise substantially similar to lead 30.

In the configuration of medical electrical lead 430, ring electrode 439 serves as the anode, thereby increasing field density adjacent anode 432 to allow for bifocal stimulation. In all other aspects, lead 430 is the same as lead 30. For brevity, details discussed with respect to lead 30 are discussed in limited or no detail with respect to lead 430.

Medical electrical lead 430 includes a central cable conductor 433 for a cathode 434, as well as a second conductor for anode 432. In some examples, the anode conductor is a coil conductor surrounding the cathode conductor within the lead body 438. In the same or different examples, the cathode conductor may be an insulated conductor, such as a solid wire, a stranded wire, or a coil conductor.

In some examples, the cathode 434 is a 0.5 to 2 mm diameter, such as 0.7 to 1 mm diameter hemispherical electrode, such as a half sphere with a diameter of about 0.87 mm, at the end of an insulated cathode conductor of the same diameter in order to provide blunt dissection. In the same or different examples, the following materials may be utilized for the helix anode 432 wire: Pt 80%/Ir 20% or Pt 90%/Ir 10% for a thinner wire. In the same or different examples, the helix coating 431 may be any suitable dielectric material, such as a polymer material, such as parylene, polymide or other non-conductive material Like lead 330, the configuration of lead 430 provides reduced anodal pacing threshold compared to lead 30. Such a configuration may be particularly useful when right septal bifocal stimulation is desired for example. A ratio of anode (ring electrode 439) to cathode surface area should be selected to support bifocal pacing. In some examples, the anode to cathode area ratio should be in 1:1 to 4:1, such as 1.5:1 to 3:1 such as about 2.3:1.

Such pacing may be useful to support LV/RV synchronization. For example, if the anode and cathode are designed to have a similar pacing capture voltage, the left bundle branch can be stimulated at the same time as the right septal myocardial (or right bundle if it were viable and in range of the anode) to promote LV/RV synchrony. The configuration of lead 430 is also suitable for His bundle pacing near the endocardial surface by prevention of cathode shorting to the helical anode as may occur with lead 30. Specifically, the location of anode ring 439 keeps the anode separated from the distal cathode 434 by the endocardial membrane. Such a configuration prevents short circuiting of the electrodes even with a shallow cathode placement. Such placement may be particularly useful when the His bundle presents near the endocardium as a shallow cathode placement would position the cathode adjacent the His bundle.

A number of modifications to the techniques described herein are within the spirit of this disclosure. For example, while the disclosed techniques are described with respect to selecting the trajectory of an electrode for His bundle pacing and LBB pacing, the leads and other techniques disclosed herein may also be used for different target sites, for cardiac pacing and otherwise.

As another example, the disclosed techniques could be used with any pulse generator, whether it is in the pectoral pocket or in the right ventricle or in conjunction with a leadless pacemaker. In this manner, the transseptal pacing techniques are suitable with any implantable pulse generator.

Various examples of this disclosure have been described. These and other examples are within the scope of the following claims.

The invention claimed is:

1. A method for implanting a medical lead comprising:
    anchoring a distal end of a lead body of the medical lead to a patient tissue proximate a target site; and
    after anchoring the distal end of the lead body to the patient tissue, extending a cable conductor along a trajectory from the distal end of the lead body to deploy a cable electrode within the patient tissue,
    wherein the cable conductor is slideable within the lead body to extend and retract the cable electrode along the trajectory extending from the distal end of the lead body,
    wherein the cable conductor includes an elongated conductor, an outer insulating layer over the elongated conductor, and the cable electrode located proximate or at a distal end of the cable conductor.

2. The method of claim 1, wherein anchoring the distal end of the lead body to the patient tissue includes anchoring a helix of the medical lead to the patient tissue proximate the target site.

3. The method of claim 1, wherein the elongated conductor is a solid wire.

4. The method of claim 1, wherein the cable conductor is slideable within the lead body to extend the cable electrode at least 1.8 centimeters from the distal end of the lead body.

5. The method of claim 1, wherein the target site is a cardiac septum of the patient.

6. The method of claim 1,
    wherein anchoring the distal end of the lead body of the medical lead to the patient tissue includes anchoring a helix of the medical lead to the patient tissue proximate a target site,
    wherein the medical lead includes:
        the lead body,
        the helix extending from the distal end of the lead body,
        a lead body electrode proximate to the distal end of the lead body, and
        the cable conductor, located within the lead body; and
    wherein, with the helix anchored to the patient tissue, extending the cable conductor along the trajectory from the distal end of the lead body includes blunt dissecting the patient tissue along the trajectory with the distal end of the cable conductor, thereby deploying the cable electrode within the patient tissue.

7. The method of claim 6, wherein the distal end of the cable conductor includes a blunt dissection tip.

8. A method for implanting a medical lead comprising:
    positioning a distal end of a catheter proximate a target site;
    delivering a distal end of the medical lead proximate the target site via the catheter;
    rotating a helix of the medical lead to anchor the helix and a distal end of a lead body of the medical lead to a patient tissue proximate the target site; and
    after anchoring the distal end of the lead body to the patient tissue with the helix, extending a cable conductor along a trajectory from the distal end of the lead body to deploy a cable electrode within the patient tissue,
    wherein the cable conductor includes an elongated conductor, an outer insulating layer over the elongated conductor, and the cable electrode located proximate or at a distal end of the cable conductor.

9. The method of claim 8, further comprising, after anchoring the helix, manipulating the catheter to set the trajectory for deploying the electrode within the patient tissue, wherein manipulating the catheter includes one or more of:
    bending the catheter through pushing and pulling from a proximal location outside the body of the patient; and
    rotating the catheter.

10. The method of claim 8, wherein the helix is fixed to the distal end of the lead body, wherein rotating the helix includes rotating the lead bod within the catheter.

11. A method for implanting a medical lead comprising:
    anchoring a distal end of a lead body of the medical lead to a patient tissue proximate a target site; and
    after anchoring the distal end of the lead body to the patient tissue, extending a cable conductor along a trajectory from the distal end of the lead body to deploy a cable electrode within the patient tissue,
    wherein deploying the electrode within the patient tissue includes blunt dissection of the patient tissue with the distal end of the cable conductor, and
    wherein the cable conductor includes an elongated conductor, an outer insulating layer over the elongated conductor, and the cable electrode located proximate or at a distal end of the cable conductor.

12. The method of claim 11, wherein the distal end of the cable conductor includes a blunt dissection tip.

13. The method of claim 12, wherein the cable electrode forms the blunt dissection tip.

14. The method of claim 12, wherein the blunt dissection tip forms a rounded frontal surface extending across a width of the cable conductor.

15. A method for implanting a medical lead comprising:
    anchoring a distal end of a lead body of the medical lead to a patient tissue proximate a target site;
    after anchoring the distal end of the lead body to the patient tissue, extending a cable conductor along a trajectory from the distal end of the lead body to deploy a cable electrode within the patient tissue; and
    after deploying the cable electrode within the patient tissue, cutting the cable adjacent a proximal end of the lead body,
    wherein the cable conductor includes an elongated conductor, an outer insulating layer over the elongated conductor, and the cable electrode located proximate or at a distal end of the cable conductor.

16. A method for implanting a medical lead comprising:
    anchoring a distal end of a lead body of the medical lead to a patient tissue proximate a target site; and
    after anchoring the distal end of the lead body to the patient tissue, extending a cable conductor along a trajectory from the distal end of the lead body to deploy a cable electrode within the patient tissue, wherein the cable conductor includes an elongated conductor, an outer insulating layer over the elongated conductor, and the cable electrode located proximate or at a distal end of the cable conductor, wherein the elongated conductor is selected from a group consisting of:
  a coil conductor; and
  a stranded wire.

17. A method for implanting a medical lead comprising:
  anchoring a distal end of a lead body of the medical lead to a patient tissue proximate a target site; and
  after anchoring the distal end of the lead body to the patient tissue, extending a cable conductor along a trajectory from the distal end of the lead body to deploy a cable electrode within the patient tissue,
  wherein the cable conductor includes an elongated conductor, an outer insulating layer over the elongated conductor, and the cable electrode located proximate or at a distal end of the cable conductor,
  wherein the medical lead includes a lead body electrode located proximate or at the distal end of the lead body.

18. The method of claim 17, wherein the medical lead further includes:
  a proximal connector including a connector pin and a ring terminal, wherein the cable electrode is electrically coupled to the connector pin via the elongated conductor; and
  a lead body conductor electrically connecting the ring terminal to the lead body electrode.

19. The method of claim 17, wherein the lead body electrode is selected from a group consisting of:
  a helical electrode; and
  a ring electrode.

20. A method for implanting a medical lead comprising:
  anchoring a distal end of a lead body of the medical lead to a patient tissue proximate a target site; and
  after anchoring the distal end of the lead body to the patient tissue, extending a cable conductor along a trajectory from the distal end of the lead body to deploy a cable electrode within the patient tissue,
  wherein the cable conductor includes an elongated conductor, an outer insulating layer over the elongated conductor, and the cable electrode located proximate or at a distal end of the cable conductor, and
  wherein the lead body has a lead body diameter of 3 to 6 French (1 to 2 mm).

21. The method of claim 20, wherein the cable conductor has a cable conductor diameter of 0.02 to 0.05 inches (0.51 to 1.27 mm).

22. The method of claim 20, wherein the cable electrode has a cable electrode diameter of between 0.5 mm and 2.0 mm.

23. A method for implanting a medical lead comprising:
  anchoring a distal end of a lead body of the medical lead to a patient tissue proximate a target site; and
  after anchoring the distal end of the lead body to the patient tissue, extending a cable conductor along a trajectory from the distal end of the lead body to deploy a cable electrode within the patient tissue,
  wherein deploying the electrode within the patient tissue comprises deploying the electrode within the patient tissue to capture a left bundle branch of the patient, and
  wherein the cable conductor includes an elongated conductor, an outer insulating layer over the elongated conductor, and the cable electrode located proximate or at a distal end of the cable conductor.

* * * * *